(12) United States Patent
Hwu et al.

(10) Patent No.: US 7,976,876 B2
(45) Date of Patent: *Jul. 12, 2011

(54) ANTI-BACTERIAL, ANTI-VIRUS, AND ANTI-FUNGUS COMPOSITION, ITS PREPARATION AND USE

(75) Inventors: Jih-ru Hwu, Taipei (TW); Shwu-chen Tsay, Taipei (TW)

(73) Assignee: Well-Being Biochemical Corp., Taipei (TW)

( * ) Notice: Subject to any disclaimer, the term of this patent is extended or adjusted under 35 U.S.C. 154(b) by 257 days.

This patent is subject to a terminal disclaimer.

(21) Appl. No.: 12/240,755

(22) Filed: Sep. 29, 2008

(65) Prior Publication Data
US 2009/0098098 A1 Apr. 16, 2009

Related U.S. Application Data

(60) Continuation of application No. 11/344,235, filed on Feb. 1, 2006, now abandoned, which is a division of application No. 10/628,259, filed on Jul. 29, 2003, now Pat. No. 7,387,799.

(51) Int. Cl.
| | |
|---|---|
| A01N 59/00 | (2006.01) |
| A01N 59/08 | (2006.01) |
| A01N 59/16 | (2006.01) |
| A01N 55/02 | (2006.01) |
| A61K 33/26 | (2006.01) |
| A61K 33/30 | (2006.01) |
| A61K 33/00 | (2006.01) |
| A61K 31/295 | (2006.01) |
| A61K 31/282 | (2006.01) |
| A61K 31/315 | (2006.01) |
| A61K 33/24 | (2006.01) |
| A61K 31/12 | (2006.01) |

(52) U.S. Cl. ...... 424/646; 424/94.1; 424/94.4; 424/601; 424/602; 424/603; 424/604; 424/641; 424/642; 424/669; 424/670; 424/671; 424/675; 424/676; 424/677; 424/678; 424/679; 424/680; 424/681; 424/686; 424/687; 424/696; 424/697; 514/492; 514/494; 514/501; 514/680; 514/681; 514/690; 514/691

(58) Field of Classification Search ............... 424/94.4, 424/646, 94.1; 514/492, 501, 690
See application file for complete search history.

(56) References Cited

U.S. PATENT DOCUMENTS

| 4,414,127 | A | 11/1983 | Fu |
| 5,330,752 | A | 7/1994 | Park et al. |
| 5,549,833 | A | 8/1996 | Hagimori et al. |
| 5,780,064 | A | 7/1998 | Meisters |
| 5,958,462 | A | 9/1999 | McLean |
| 6,169,110 | B1 * | 1/2001 | Fulton, Jr. .................... 514/460 |
| 6,664,289 | B2 | 12/2003 | Hansen |
| 6,753,016 | B2 | 6/2004 | Ghosh |
| 7,585,826 | B2 * | 9/2009 | Hwu et al. .................... 510/110 |

FOREIGN PATENT DOCUMENTS

| EP | 0 109 279 | 5/1984 |
| JP | 2000-226398 | 8/2000 |
| JP | 2001-39809 | 2/2001 |
| JP | 2002-284667 | 10/2002 |
| WO | 94/01143 | 1/1994 |
| WO | 94/04167 | 3/1994 |
| WO | 94/09798 | 5/1994 |
| WO | 96/02624 | 2/1996 |
| WO | 99/63816 | 12/1999 |

OTHER PUBLICATIONS

Elzanowska, et al., "Bactericidal Properties of Hydrogen Peroxide and Copper or Iron-Containing Complex Ions in Relating to Leukocyte Function", Free Radical Biology & Medicine, vol. 18, No. 3, pp. 437-449, 1995.

Reed, et al., "Chemical Cleavage of Plasmid DNA by Glutathione in the Presence of Cu(II) ions", Biochem. J. (1991) 275, 601-608.

Rodriguez, et al., Mapping of Copper/Hydrogen Peroxide-induced DNA Damage at Nucleotide Resolution in Human Genomic DNA by Ligation-mediated Polymerase Chain Reaction, The Journal of Biological Chemistry (Jul. 1995), vol. 270, No. 29, pp. 17633-17640.

Oikawa, et al., "Site-Specific DNA Damage Induced by NADH in the Presence of Copper (II): Role of Active Oxygen Species", Biochemistry (1996), 35 (14), pp. 4584-4590.

HCAPLUS abstract 2002:570068 (2002).
HCAPLUS abstract 2003:206436 (Mar. 2003).

(Continued)

Primary Examiner — John Pak
(74) Attorney, Agent, or Firm — Occhiuti Rohlicek & Tsao LLP

(57) ABSTRACT

The present invention relates to an anti-bacterial, anti-virus, and anti-fungus composition, its preparation and use. The composition of the present invention mainly includes the following three ingredients in an adequate ratio: (A) a metal compound having a catalytic function; (B) a mixture of a coenzyme having reducing ability and a quinone, and (C) an additive. The anti-bacterial, anti-virus, and anti-fungus composition of the present invention is capable of destroying viruses as well as killing bacterial and fungi. Therefore, the composition can be formulated as an aerosol and a film for applying to protection devices such as respirators, masks, gloves, filters, condoms, etc. The present composition can also be used in household, vehicle, hospital, school, restaurant, hotel, internet coffee shop for applying to filter of air-conditioner, tap, stool, interior of elevator and its keyboard. Additionally, the present composition can be applied to human being such as applying to hand, foot, genital organs, oral cavity, and the like in a lower dose to attain the effect of destroying of bacteria, viruses, and fungi.

6 Claims, 2 Drawing Sheets

OTHER PUBLICATIONS

Medline abstract 85057613 (1990).
Medline abstract 2001149154 (2001).
Medline abstract 2002276939 (2002).
Hydrogen Peroxide Material Safety Data Sheet, Boston University, Retrieved from the internet on Aug. 20, 2007, URL< http://www.bu.edu/es/labsafety/ESMSDSs/MSHydPeroxide.html>. Jan. 23, 1998.
Database CAPLUS 'Online! Chemical Abstracts Service, Columbus, Ohio, US; 1996; Goncharuk, et al; Disinfection by Hydrogen Peroxide in the Presence of Metal Ions Catalyzing Its Decomposition; Database Accession No. XP002280640; Dopovidi Natsional 'Noi Akademii Nauk Ukraini No. 6, 1995, pp. 123-127.
Database Caplus 'Online! Chemical Abstracts Service, Columbus, Ohio, US 1993; Luo, Yongzhen, et al; Formulations of Disinfectants Containing Hydrogen Peroxide and Zinc Acetate for Wounds; Database Accession No. 1993-15406 XP002280641; CN 1 065 204 A; Chengdu College of Traditional Chinese Medicine; Oct. 14, 1992.
Patent Abstracts of Japan; vol. 2002, No. 06; Jun. 4, 2002 & JP 2002 060375 A (Fujii Kenji) Feb. 26, 2002 *Abstract*; Method for producing Amino Acid Metal Phosphate.
Database WPI; Week 199328; Derwent Publications Ltd., London, GB; XP002280642 & JP 05 148116 A (Sumitomo Cement Co.; Jun. 15, 1993 *Abstract*.
Database WPI; Week 199513; Derwent Publications Ltd., London, GB; AN 1995-093713 XP002280643 & JP 07 017903 A (Shiraishi Chuo Kenkyusho KK), Jan. 20, 1995 *abstract*.
JPAB Abstract 02002284667A, abstracting JP 2002-284667 (Oct. 2002).

* cited by examiner

ANTI-BACTERIAL, ANTI-VIRUS, AND ANTI-FUNGUS COMPOSITION, ITS PREPARATION AND USE

RELATED APPLICATION

This application is a continuation of and claims priority to U.S. patent application Ser. No. 11/344,235, filed Feb. 1, 2006, which in turn is a division of and claims priority to U.S. patent application Ser. No. 10/628,259, filed Jul. 29, 2003, The contents of the two applications are herein incorporated by reference.

FIELD OF THE INVENTION

The present invention provides an anti-bacterial, anti-virus and anti-fungus composition, its preparation and use. The composition of the present invention mainly includes the following three ingredients in an adequate ratio: (A) a metal ionic compound having catalytic function; (B) ionic compound, sulfur compound, coenzyme having reducing ability, or an agent having oxidizing ability; and (C) an additive. The anti-bacterial, anti-virus, and anti-fungus composition of the present invention can attain the effect of destroying and killing of bacteria, viruses, and fungi when it contacts with them.

BACKGROUND OF THE INVENTION

Severe Acute Respiratory Syndrome (SARS) virus is first found in China and rapidly spread over Asia, Europe, North America, etc. It is commonly considered that people are infected with the virus through breathing in flying particles of saliva and phlegm of a patient affected such a disease. With increasing of mortality and serious cases, people need respirator to protect themselves from the infection while doctors and nurses need to wear protection suit in addition to the respirator. However, the current used respirators and protection suit can only inhibit virus invading into respiratory system of human with no function of destroying bacteria and viruses. As a filter used in air-conditioner, it has only been developed to possess functions of air cleaning as well as bactericidal and fungicidal effects. Few virus still affect human to cause serious disease and may cause human death if virus pass through protection devices such as respirators and protection suit. At present, examples of respirators include industrial respirator N95 passed the standard regulated by United States, industrial respirator FEP1 and FEP2 passed the standard regulated by European Community, medical respirator having activated carbon, general medical respirator, etc. Among them, although the N95 respirator, which is considered possessing more protection effect, can filter out about 95% non-oily particles in air, it possesses no functions of destroying viruses and bacteria.

SUMMARY OF THE INVENTION

The present invention provides an anti-bacterial, anti-virus, and anti-fungus composition, which mainly includes the following three ingredients in an adequate ratio: (A) a metal ionic compound having catalytic function; (B) ionic compound, sulfur compound, coenzyme having reducing ability, or an agent having oxidizing ability; and (C) an additive.

The present invention also provides a method for preparing an anti-bacterial, anti-virus, and anti-fungus composition and the use of the composition.

The term "bacteria" used herein includes various bacteria. The term "viruses" used herein includes any kind of viruses, such as SARS virus, AIDS virus, orthopoxviruses (vaccinia, cowpox, monkey pox), biodefense (west nile), hepatitis B virus, hepatitis C virus, respiratory viruses (influenza A and B, corona), herpesviruses (HSV-1, HSV-2, VZV) etc.

The terms "fungi" and "fungus" used herein include various fungi.

The anti-bacterial, anti-virus, and anti-fungus composition according to present invention can be formulated in various dosage forms such as spray, aerosol, and film at various concentrations. Among them, a film form of the present composition is useful to manufacture biochemical protective respirator, biochemical protective mask, biochemical protective suit, biochemical filter, etc. When bacteria and viruses, such as SARS virus, contained in saliva pass the film produced from the anti-bacterial and anti-virus composition of the present invention, it will be destroyed by the ingredients contained in the present composition and thus lose its infective ability.

These and other features, objects and advantages will be obvious by those skilled in the art from the following detailed description and appended claims.

DETAILED DESCRIPTION OF THE PRESENT INVENTION

Figure 1:
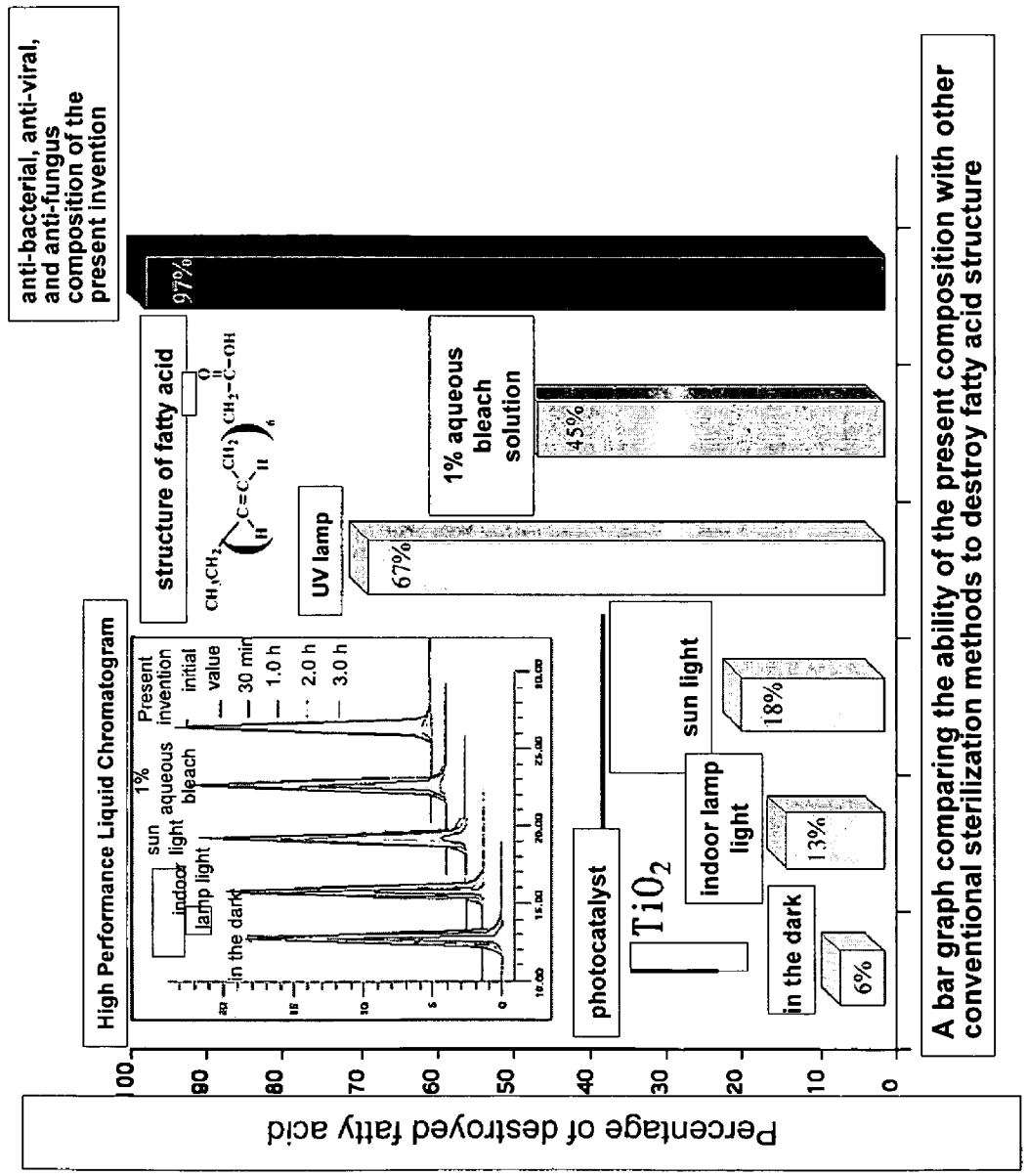
FIG. 1 shows a bar graph comparing an ability of the present composition with other conventional sterilization methods to destroy fatty acid structure carried out in Biological Experiment Example 1.

The present invention provides an anti-bacterial, anti-virus, and anti-fungus composition, which can be formulated in various dosage forms, such as spray, aerosol, and a film. The dosage form of spray and aerosol can be used in household, vehicle, hospital, school, restaurant, hotel, internet coffee shop for applying to filter of air-conditioner, tap, stool, interior of elevator and its keyboard. Additionally, the present composition can be applied to human being such as hand, foot, genital organs, oral cavity, and the like in a lower dose to attain the effect of destroying bacteria, viruses, and fungi. The anti-bacterial, anti-virus, and anti-fungus composition consists of three ingredients at various ratio and concentration, and can be formulated in various dosage forms.

The ingredient (A) used in the anti-bacterial, anti-virus, and anti-fungus composition is a metal ionic compound having a catalytic function, which has a general formula $M_bX_a$, in which M is a metal element selected from the group consisting of Ni, Co, Mg, Mn, Cr, Ca, Fe, Cu, Ti, Al, Sb, Sn, Pb, Zn, Pt, Pd, Os, Ru, Cd, Rh, and Ir, or M is $NH_4$; X is an anionic group selected from the group consisting of fluoride, chloride, bromide, iodide, nitrate, sulfate, sulfite, acetate, oxalate, carboxylate, succinate, phosphate, pyrophosphate, perchlorate, gluconate, ascorbate, ethylenediamine tetraacetate, fumarate, and lactate; a is an integer of from 1 to 6; and b is an integer of from 1 to 6.

The ingredient (B) used in the anti-bacterial, anti-virus, and anti-fungus composition is a mixture of a coenzyme having reducing ability and an agent having oxidizing ability. Examples of the coenzyme having reducing ability include, but not limit to, reduced flavin mononucleotide ($FMNH_2$), reduced flavin adenine dinucleotide ($FADH_2$), reduced nicotinamide adenine dinucleotide (NADH), and reduced nicotinamide adenine dinucleotide phosphate (NADPH). Also, examples of the agent having oxidizing ability include, but not limit to, hydrogen peroxide, quinones such as azulenequinone and its derivatives.

The ingredient (C) used in the anti-bacterial, anti-virus, and anti-fungus composition is an additive having a general formula $R_dY_z$, in which R is an element selected from the group consisting of Li, Na, K, Mg, Ca, and Zn; Y is selected from the group consisting of chloride, nitrate, sulfate, carboxylate, carbonate, bicarbonate, phosphate, dihydrogen phosphate, hydrogen phosphate, and oxalate; d is 1, 2 or 3; and z is 1 or 2.

The weight ratio of ingredients (A):(B):(C) is 1:10-50:1500-3000, preferably 1:15-25:2000-2500.

The term "$C_1$ to $C_6$ alkyl group" used herein means a straight or branched alkyl chain having 1 to 6 carbon atoms. Examples of the $C_1$ to $C_6$ alkyl include, but not limit to, methyl, ethyl, n-propyl, i-propyl, n-butyl, s-butyl, t-butyl, pentyl, hexyl and the like.

The term "aryl group" used herein means a $C_{6-14}$ aromatic group. Examples of the aryl group include, but not limit to, phenyl, naphthyl, anthryl, and its derivatives.

The term "aralkyl group" used herein means a $C_1$ to $C_6$ alkyl group defined above bonded via an aryl group defined above.

In one embodiment of the present invention, the ingredient (A) is a Ni, Co, or Pd ionic compound, and the ingredient (B) is a mixture of a coenzyme having reducing ability and a quinone. In this embodiment, the anti-bacteria, anti-virus, and anti-fungus composition of the present invention includes the following ingredients:

(A) a metal ionic compound having a catalytic function, which has a formula $M_bX_a$, in which M is a metal element selected from the group consisting of Ni, Co, and Pd; X is an anionic group selected from the group consisting of fluoride, chloride, bromide, iodide, nitrate, sulfate, sulfite, acetate, oxalate, carboxylate, succinate, phosphate, pyrophosphate, perchlorate, gluconate, ascorbate, ethylenediamine tetraacetate, fumarate, and lactate; a is an integer of from 1 to 6; and b is an integer of from 1 to 6;

(B) a mixture of a coenzyme having reducing ability and a quinone; and (C) an additive having a formula $R_dY_z$, in which R is an element selected from the group consisting of Li, Na, K, Mg, Ca, and Zn; Y is selected from the group consisting of chloride, nitrate, sulfate, carboxylate, carbonate, bicarbonate, phosphate, dihydrogen phosphate, hydrogen phosphate, and oxalate; d is 1, 2 or 3; and z is 1 or 2; wherein the weight ratio of ingredients (A):(B):(C) is 1:10-50:1500-3000.

In another one specific embodiment of the present invention, the coenzyme having reducing ability in ingredient (B) is selected from the group consisting of reduced flavin mononucleotide (FMNH2), reduced flavin adenine dinucleotide (FADH2), reduced nicotinamide adenine dinucleotide (NADH), and reduced nicotinamide adenine dinucleotide phosphate (NADPH).

The anti-bacterial, anti-virus, and anti-fungus composition of the present invention can destroy protein, RNA, DNA and sheaf of bacteria and viruses. If the composition is applied on respirator, mask, filter, condom, and other protection devices, it can destroy protein, RNA, DNA and sheaf of bacteria and viruses to allow the bacteria and viruses losing its infectious ability when they pass the protection devices on which the present composition is applied. Therefore, the anti-bacterial, anti-virus, anti-fungus composition of the present invention can inhibit the bacteria and virus entering the respiratory system or lower their quantities to prevent from contacting with the skin of human beings and can attain the protection purpose for preventing human and environment from being infected by bacteria and viruses. If the present composition is used in a dosage form of spray or aerosol, it can spray on surface of target to attain the above protection purposes.

When the anti-bacterial, anti-virus, and anti-fungus composition of the present invention is sprayed on a respirator and mask, its anti-bacteria, anti-virus, and anti-fungus effects remain up to 8 hours. When the anti-bacterial, anti-virus, and anti-fungus composition of the present invention is used in filter of air-conditioners, its effect remains about from 3 to 14 days. If the present composition is applied to other protection devices, its effect may remain from 12 to 72 hours depending on conditions of environment. The present composition is not edible, but it is not harmful to human when the present composition is applied to respirator, mask, gloves, filter, condom, and other protection devices.

The present invention is further illustrated with references to the following examples and experiment examples. However, any modification and change can be made by those skilled in the art without departing from the spirit and scope of the above description and following claims.

Example 1

The anti-bacteria, anti-virus, and anti-fungus composition of the present invention is prepared as follows.

Preparation of ingredient A: 0.10 gram of cuprous chloride was added to 10 liters of Reverses Osmosis (R.O.) water. The mixture was stirred at room temperature for 30 minutes to form a clear solution without precipitation, which the clear solution is referred to as ingredient A.

Preparation of ingredient B: 5.0 ml of 3% hydrogen peroxide solution was added to 10 liters of R.O. water and then 5.0 grams of coenzyme NADPH were added thereto. The mixture was stirred at room temperature for 20-30 minutes until a homogenous solution was formed. Then 8.0 mg of azulenequinone derivative was added thereto and stirred for about 2.0 hours until the opaque solution become a clear solution, which is referred to as ingredient B.

Preparation of ingredient C: 80 grams of sodium chloride and 60 grams of sodium bicarbonate were added into 980 liters of R.O. water in sequence and stirred until solutes were dissolved completely. Then 10 grams of potassium hydrogen phosphate, 10 grams of potassium dihydrogen phosphate, and 15 grams of calcium sulfate and 10 grams of magnesium chloride were added thereto in sequence while the mixture was stirred vigorously at room temperature for 4.0 hours until no suspension was observed. The resultant solution is referred to as ingredient C.

Ingredient A was added into ingredient C and the mixture was stirred at room temperature for 20-30 minutes. Then ingredient B was added into the mixture and stirred for 10-20 minutes. The resultant composition was filled in a closed container in the absence of air. The closed container is equipped with a valve to spray the composition onto respirator, mask, gloves, filter, condom and other protection devices. In this case, the concentration of the composition is about $10^{-7}$ to $10^{-8}$% by weight. In the case of applying to human beings, the concentration of the composition is about $10^{-9}$ to $10^{-10}$% by weight.

Biological Experiment Example 1

This experiment example is used to demonstrate the ability of the present composition to destroy virus and is carried out by mimic experiments. The experiment uses fatty acid having a structure shown in FIG. 1 to mimic lipid membrane of virus and use φX174 RFI DNA to mimic RNA of viruses. The fatty acid was allowed to react with 100 μL of the present composition prepared in Example 1 for 30 minutes and its anti-virus effect was analyzed by using High Performance Liquid Chromatography (HPLC). The result was compared with those obtained by using 1% aqueous bleach solution, photocatalyst $TiO_2$ associated with sun light, with ultraviolet (UV) light, with lamp light, and in the dark. The results are summarized in FIG. 1.

From the results listed in FIG. 1, it is known that the anti-bacteria, anti-virus, and anti-fungus composition of the present invention destroyed up to 97% of fatty acid in 30 minutes, which is greatly better than the conventional anti-bacteria and anti-virus method.

Biological Experiment Example 2

This experiment example is used to demonstrate the ability of the present composition to destroy nucleic acids. In this experiment, DNA (50 μM/base pair, 1.0 μL) was allowed to react with 100 μL of the present composition prepared in Example 1. The amount of Form TI and Form III resulting from the reaction was determined by using electrophoresis and destroying percentage of the nucleic acids was calculated to be up to 99%. The result was also compared with those obtained by using 1% aqueous bleach solution, photocatalyst $TiO_2$ associated with sun light, with ultraviolet (UV) light, with lamp light, and in the dark. The results are summarized in FIG. 2.

Figure 2:
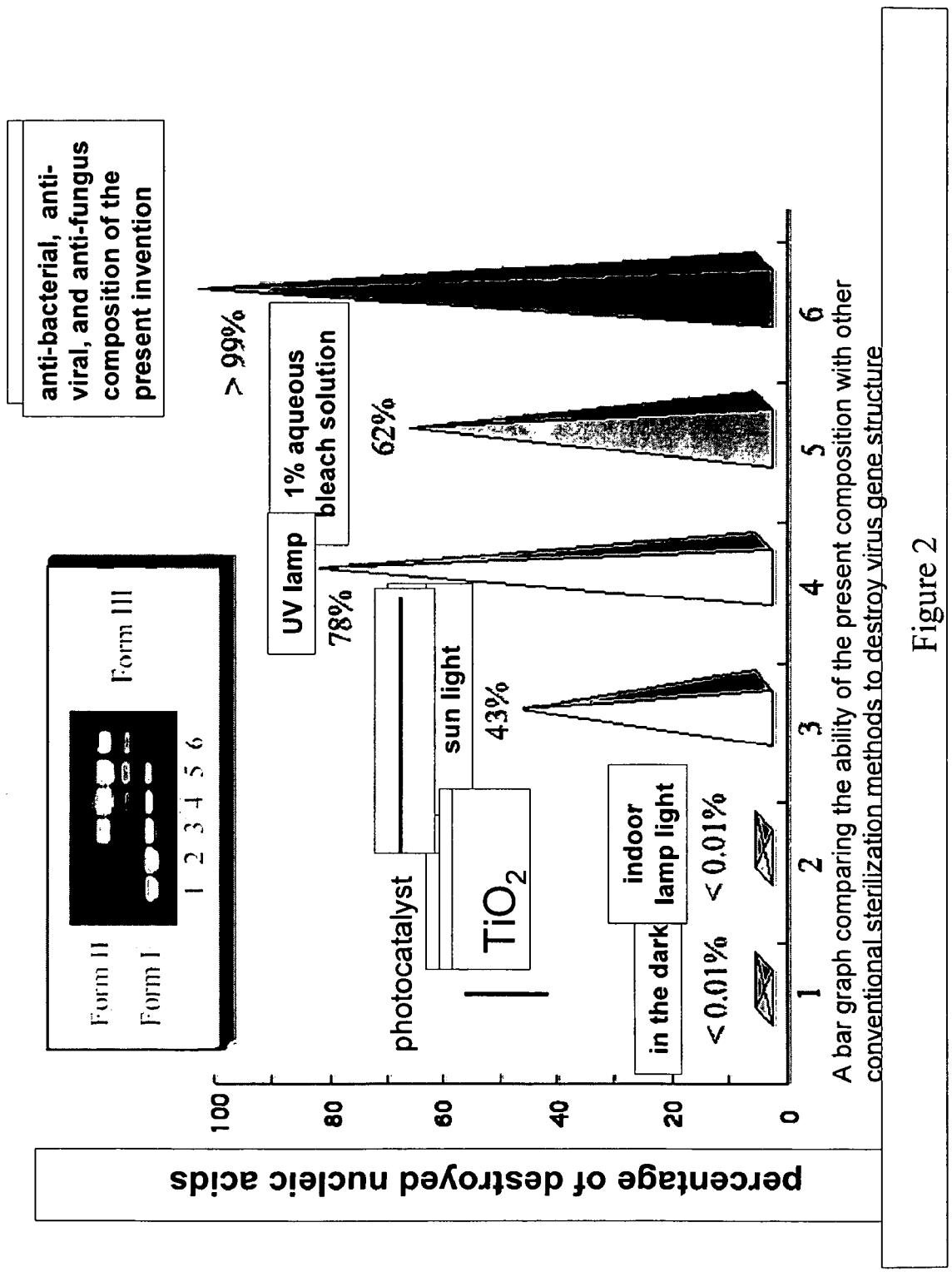
FIG. 2 shows a bar graph comparing an ability of the present composition with other conventional sterilization methods to destroy virus gene structure carried out in Biological Experiment Example 2.

From the results listed in FIG. 2, it is known that the anti-bacteria and anti-virus composition of the present invention destroyed up to 99% of nucleic acids, which is greatly better than the conventional anti-bacteria and anti-virus method.

Although the present invention has been illustrated with references to the above detailed description, the description and the above examples and experiment examples are used to only illustrate the present invention without limiting the scope of the invention. Any modification, change, and equivalence could be made by persons skilled in the art without departing from the spirit and scope of the present invention.

What is claimed is:

1. An anti-bacteria, anti-virus, and anti-fungus composition, which includes the following ingredients:
   (A) a metal ionic compound having a catalytic function, which has a formula $M_bX_a$, in which M is a metal element selected from the group consisting of Ni, Co, and Pd; X is an anionic group selected from the group consisting of fluoride, chloride, bromide, iodide, nitrate, sulfate, sulfite, acetate, oxalate, carboxylate, succinate, phosphate, pyrophosphate, perchlorate, gluconate, ascorbate, ethylenediamine tetraacetate, fumarate, and lactate; a is an integer of from 1 to 6; and b is an integer of from 1 to 6;
   (B) a mixture of a coenzyme having reducing ability and a quinone; and
   (C) an additive having a formula $R_dY_z$, in which R is an element selected from the group consisting of Li, Na, K, Mg, Ca, and Zn; Y is selected from the group consisting of chloride, nitrate, sulfate, carboxylate, carbonate, bicarbonate, phosphate, dihydrogen phosphate, hydrogen phosphate, and oxalate; d is 1, 2 or 3; and z is 1 or 2; wherein the weight ratio of ingredients (A):(B):(C) is 1:10-50:1500-3000.

2. The anti-bacteria, anti-virus, and anti-fungus composition according to claim 1, wherein the coenzyme having reducing ability in ingredient (B) is selected from the group consisting of reduced flavin mononucleotide (FMNH2), reduced flavin adenine dinucleotide (FADH2), reduced nicotinamide adenine dinucleotide (NADH), and reduced nicotinamide adenine dinucleotide phosphate (NADPH).

3. The anti-bacteria, anti-virus, and anti-fungus composition according to claim 1, which is formulated as a spray, aerosol, and a film.

4. The anti-bacteria, anti-virus, and anti-fungus composition according to claim 1, which is used in household, vehicle, hospital, school, restaurant, hotel, internet coffee shop for applying to filter of air-conditioner, tap, stool, interior of elevator and its keyboard, and for applying to human beings.

5. A method for producing an anti-bacteria, anti-virus, and anti-fungus composition according to claim 1, which includes the step of mixing the following ingredients:
   (A) a metal ionic compound having a catalytic function, which has a formula $M_bX_a$, in which M is a metal element selected from the group consisting of Ni, Co, and Pd; X is an anionic group selected from the group consisting of fluoride, chloride, bromide, iodide, nitrate, sulfate, sulfite, acetate, oxalate, carboxylate, succinate, phosphate, pyrophosphate, perchlorate, gluconate, ascorbate, ethylenediamine tetraacetate, fumarate, and lactate; a is an integer of from 1 to 6; and b is an integer of from 1 to 6;
   (B) a mixture of a coenzyme having reducing ability and a quinone; and
   (C) an additive having a formula $R_dY_z$, in which R is an element selected from the group consisting of Li, Na, K, Mg, Ca, and Zn; Y is selected from the group consisting of chloride, nitrate, sulfate, carboxylate, carbonate, bicarbonate, phosphate, dihydrogen phosphate, hydrogen phosphate, and oxalate; d is 1, 2 or 3; and z is 1 or 2; wherein the weight ratio of ingredients (A):(B):(C) is 1:10-50:1500-3000.

6. The method according to claim 5, wherein the coenzyme having reducing ability in ingredient (B) is selected from the group consisting of reduced flavin mononucleotide (FMNH2), reduced flavin adenine dinucleotide (FADH2), reduced nicotinamide adenine dinucleotide (NADH), and reduced nicotinamide adenine dinucleotide phosphate (NADPH).

* * * * *